(12) United States Patent
Fujikura

(10) Patent No.: US 8,721,526 B2
(45) Date of Patent: May 13, 2014

(54) INSERTION ASSISTING DEVICE AND ENDOSCOPE APPARATUS

(75) Inventor: Tetsuya Fujikura, Saitama (JP)

(73) Assignee: Fujinon Corporation, Saitama-shi (JP)

( * ) Notice: Subject to any disclaimer, the term of this patent is extended or adjusted under 35 U.S.C. 154(b) by 0 days.

(21) Appl. No.: 13/460,225

(22) Filed: Apr. 30, 2012

(65) Prior Publication Data

US 2012/0220829 A1    Aug. 30, 2012

Related U.S. Application Data

(62) Division of application No. 12/138,337, filed on Jun. 12, 2008, now abandoned.

(30) Foreign Application Priority Data

Jul. 18, 2007  (JP) .............................. P2007-187156
Jul. 18, 2007  (JP) .............................. P2007-187157

(51) Int. Cl.
*A61B 1/00* (2006.01)

(52) U.S. Cl.
USPC ........... 600/115; 600/130; 600/132; 600/153; 600/156

(58) Field of Classification Search
USPC ................................................ 600/121–125
See application file for complete search history.

(56) References Cited

U.S. PATENT DOCUMENTS

| | | | |
|---|---|---|---|
| 3,599,639 A | 8/1971 | Spotz | |
| 3,835,842 A | 9/1974 | Iglesias | |
| 4,198,958 A | 4/1980 | Utsugi | |
| 4,667,655 A | 5/1987 | Ogiu et al. | |
| 4,760,838 A | 8/1988 | Fukuda | |
| 4,991,565 A * | 2/1991 | Takahashi et al. | 600/123 |
| 5,050,585 A * | 9/1991 | Takahashi | 600/123 |
| 5,105,800 A * | 4/1992 | Takahashi et al. | 600/121 |
| 5,201,908 A * | 4/1993 | Jones | 600/123 |
| 5,334,183 A | 8/1994 | Wuchinich | |
| 5,359,991 A * | 11/1994 | Takahashi et al. | 600/122 |
| 5,441,503 A | 8/1995 | Considine et al. | |

(Continued)

FOREIGN PATENT DOCUMENTS

| | | |
|---|---|---|
| CN | 1636499 A | 7/2005 |
| DE | 201 17 907 | 2/2002 |

(Continued)

OTHER PUBLICATIONS

Corresponding Chinese Office Action issued May 11, 2010 in Chinese application No. 200810127428.7 (with English translation).

(Continued)

*Primary Examiner* — Matthew J Kasztejna
(74) *Attorney, Agent, or Firm* — Birch, Stewart, Kolasch & Birch, LLP

(57) ABSTRACT

An insertion assisting device 60 has an insertion path 70 into which an insertion portion 12 of an endoscope 100 is inserted and has a substantially tubular shape. The insertion assisting device 60 includes a ventilation opening 90 that is formed on a distal-end surface or outer circumferential surface thereof, a ventilation duct 74 that communicates with the opening 90 and is different from the insertion path 70, and a liquid reservoir tank 116 that is connected to a base-end side of the duct 74 and stores liquid flowing out of the duct 74.

3 Claims, 14 Drawing Sheets

(56) References Cited

U.S. PATENT DOCUMENTS

| | | |
|---|---|---|
| 5,460,610 A | 10/1995 | Don Michael |
| 5,924,977 A * | 7/1999 | Yabe et al. .................... 600/121 |
| 6,110,104 A * | 8/2000 | Suzuki et al. ................. 600/124 |
| 6,248,086 B1 | 6/2001 | Sweezer et al. |
| 6,461,327 B1 | 10/2002 | Addis et al. |
| 6,533,720 B1 * | 3/2003 | Dhindsa ........................ 600/159 |
| 6,599,237 B1 | 7/2003 | Singh |
| 2002/0014238 A1 | 2/2002 | Kotmel |
| 2003/0083547 A1 * | 5/2003 | Hamilton et al. ............. 600/116 |
| 2003/0122374 A1 | 7/2003 | Ouchi et al. |
| 2005/0137457 A1 | 6/2005 | Machida |
| 2005/0215856 A1 | 9/2005 | Fujikura |
| 2006/0241348 A1 | 10/2006 | Kohno |
| 2007/0142702 A1 | 6/2007 | Haller et al. |
| 2007/0232853 A1 | 10/2007 | Yamaya |
| 2008/0082084 A1 | 4/2008 | Roberts et al. |

FOREIGN PATENT DOCUMENTS

| | | |
|---|---|---|
| EP | 1 547 640 A1 | 6/2005 |
| EP | 1 547 641 A2 | 6/2005 |
| EP | 1 576 918 A1 | 9/2005 |
| EP | 1 707 107 A1 | 10/2006 |
| EP | 1 989 994 A | 11/2008 |
| JP | 1-120802 | 8/1989 |
| JP | 6-66613 | 9/1994 |
| JP | 10-262907 A | 10/1998 |
| JP | 2000-189378 A | 7/2000 |
| JP | 2002-301019 A | 10/2002 |
| JP | 2005-9176 A | 1/2005 |
| JP | 3804068 | 8/2005 |
| JP | 2005-270216 A | 10/2005 |
| JP | 2005-296617 A | 10/2005 |
| JP | 2005-334678 A | 12/2005 |
| JP | 2006-280535 A | 10/2006 |

OTHER PUBLICATIONS

Corresponding European Office Action issued May 18, 2010 in European application No. 08 011 732.8-2319.

Japanese Office Action, dated Dec. 2, 2011, for Japanese Application No. 2007-187157, including English translation.

Office Action in Japanese Application No. 2007-187156, dated Jan. 24, 2012, including an English translation.

European Office Action for European Application No. 08011732.8, dated Aug. 1, 2013.

* cited by examiner

INSERTION ASSISTING DEVICE AND ENDOSCOPE APPARATUS

CROSS-REFERENCE TO RELATED APPLICATIONS

This application is a Divisional of application Ser. No. 12/138,337 filed on Jun. 12, 2008 now abandoned, and for which priority is claimed under 35 U.S.C. §120; and this application claims priority from the Japanese Patent Application Nos. 2007-187156 and 2007-187157 both filed on Jul. 18, 2007; the entire contents of which are incorporated herein by reference.

BACKGROUND OF THE INVENTION

1. Technical Field

The invention relates to an insertion assisting device and an endoscope apparatus, and more specifically, to a medical insertion assisting device which assists an endoscope for observing the small or large intestine or the like to be inserted into the body, and a medical endoscope apparatus for observing the small or large intestine or the like through the endoscope.

2. Description of the Related Art

The deep digestive tract such as the small intestine or the large intestine is complexly bent. Therefore, if an insertion portion of an endoscope is merely pushed, the pushing force is hardly transmitted to the distal end of the insertion portion, which makes it difficult to insert the insertion portion into the deep digestive tract. Therefore, there has been proposed a method of inserting the insertion portion of the endoscope into a tubular insertion assisting device (referred to as an over-tube or a sliding tube) so as to be inserted into the body. According to this method, the insertion portion is guided by the insertion assisting device. Therefore, the insertion portion can be prevented from being unnecessarily bent or flexed, which makes it possible to insert the insertion portion to the deep portion of the digestive tract.

JP 2002-301019 A discloses an endoscope apparatus in which a balloon is provided on a distal-end portion of an insertion portion of an endoscope and another balloon is provided on a distal-end portion of an insertion assisting device. According to this endoscope apparatus, the insertion portion and/or the insertion assisting device can be fixed to the digestive tract by inflating the balloon. Further, while the balloon is repeatedly inflated and deflated, the insertion portion and the insertion assisting device are alternately inserted. Then, the insertion portion can be inserted to the deep portion of the digestive tract.

In the endoscope apparatus of JP 2002-301019 A, however, if the insertion assisting device is moved in a withdrawal direction in a state where the balloon of the insertion assisting device is inflated and is in close contact with the intestine wall, it is difficult to move the insertion assisting device smoothly. This is because the air being accumulated in the base-end side of the balloon of the insertion assisting device is compressed such that the air pressure interferes with the withdrawal operation of the insertion assisting device.

To solve such a problem, Japanese Patent No. 3804068 (corresponding to US 2005/0137457 A) discloses an insertion assisting device that includes a ventilation hole provided in a position that is closer to the base-end side than a mounting position of a balloon, the ventilation hole communicating with the outside through an air insertion duct that is different from an insertion path for an insertion portion of an endoscope. According to this insertion assisting device, if the insertion assisting device is withdrawn in a state where a second balloon is inflated, the air accumulated between the insertion assisting device and the intestine wall is discharged from the ventilation hole to the outside through the air insertion duct. Therefore, the withdrawal operation of the insertion assisting device can be smoothly performed.

In the insertion assisting device of Japanese Patent No. 3804068, however, if the section area of the air insertion duct is increased to secure ventilation, liquid such as body fluid easily enters the air insertion path. Then, the liquid may leak from the end portion of the air insertion path and may contaminate a working region. Furthermore, the liquid entering the air insertion path may flow backward into the body depending on a pressure change in the vicinity of the ventilation hole.

SUMMARY OF THE INVENTION

The invention has been made in view of the above circumstances and provides an insertion assisting device that can prevent liquid such as body fluid from flowing out of a ventilation duct and from contaminating a working region.

Also, the invention may provide an endoscope apparatus in which a ventilation hole of an insertion assisting device is connected to a suction device such that suction can be reliably performed, the endoscope apparatus having good operability.

[1] According to one aspect of the invention, an insertion assisting device has a substantially tubular shape. The insertion assisting device includes an insertion path, a ventilation hole, a ventilation duct and a liquid storage unit. An insertion portion of an endoscope is inserted into the insertion path. The ventilation hole is formed on a distal-end surface or outer circumferential surface of the insertion assisting device. The ventilation duct communicates with the ventilation hole and is different from the insertion path. The liquid storage unit is connected to a base-end side of the ventilation duct and stores liquid flowing out of the ventilation duct.

With the configuration of [1], since the liquid storage unit (trap) is provided, liquid such as body fluid flowing out of the ventilation duct is stored in the liquid storage unit. Therefore, it is possible to prevent the liquid such as the body fluid from leaking and contaminating a working region.

[2] In the insertion assisting device of [1], the liquid storage unit may be a liquid reservoir tank. The liquid reservoir tank may include a pipe and a discharge path. The pipe has one end that communicates with the ventilation duct, and the other end that is disposed in the liquid reservoir tank. Gas within the tank is discharged through the discharge path.

With the configuration of [2], the liquid such as the body fluid flowing into the ventilation duct flows through the pipe so as to be stored in the liquid reservoir tank, and the gas within the liquid reservoir tank is discharged through the discharge path. Therefore, only liquid in the fluid flowing into the ventilation duct can be stored in the liquid reservoir tank.

[3] In the insertion assisting device of [1] or [2], the liquid storage unit may be detachably mounted on a grasp portion of the insertion assisting device.

With the configuration of [3], since the liquid storage unit is detachably mounted on the grasp portion of the insertion assisting device, a connection tube is not necessary, which makes it possible to enhance the operationality of the insertion assisting device.

[4] In the insertion assisting device of any one of [1] to [3], a check valve for preventing a flow from the base-end side of the ventilation duct to a distal-end side of the ventilation duct may be provided in the ventilation duct or a duct communicating with the ventilation duct.

With the configuration of [4], since the check valve is provided, the liquid such as the body fluid flowing into the ventilation duct can be prevented from flowing backward and leaking from the ventilation hole.

[5] In the insertion assisting device of any one of [1] to [3], the ventilation duct may be connected to a suction device through the liquid storage unit.

With the configuration of [5], the fluid can be forcibly suctioned from the ventilation hole by the suction device. In this case, since the forcibly-suctioned liquid is also stored in the liquid storage unit, a working region can be prevented from being contaminated.

[6] In the insertion assisting device of [5], an opening that communicates with a portion diverging from the ventilation duct may be formed in a grasp portion of the insertion assisting device.

With the configuration of [6], the ventilation duct is opened to the outside through the opening of the grasp portion. Therefore, even if a suction force is applied to the ventilation duct, the suction from the ventilation hole is not performed. Furthermore, when the opening of the grasp portion is closed, the ventilation duct is blocked from outside. Therefore, the suction from the ventilation hole can be performed in this state by applying a suction force to the ventilation duct. Accordingly, with the configuration of [6], when an operator grasps the grasp portion of the insertion assisting device and closes the opening or releases the closing, the operator can switch between the suction from the ventilation hole and the stop of the suction.

[7] In the insertion assisting device of any one of [1] to [6], the liquid storage unit may include a liquid holding unit that holds the stored liquid therein.

With the configuration of [7], since the liquid storage unit includes the liquid holding unit, the stored liquid can be prevented from leaking to the outside. Furthermore, an absorption member, such as a sponge or an absorbent sheet, which absorbs liquid or a polymer which gelatinizes or solidifies liquid may be used as the liquid holding unit.

[8] In the insertion assisting device of any one of [1] to [7], an inflatable balloon may be mounted on the outer circumference of the distal-end portion of the insertion assisting device.

With the configuration of [8], since the balloon is mounted on the outer circumference of the distal-end portion of the insertion assisting device, the distal-end portion of the insertion assisting device can be fixed to the inside of the body by inflating the balloon. Furthermore, if the insertion assisting device is withdrawn while the balloon inflates, the air accumulated in the body can be discharged to the outside from the ventilation hole through the ventilation duct. Therefore, it is possible to smoothly withdraw the insertion assisting device.

[9] According to another aspect of the invention, an endoscope apparatus includes an endoscope having an insertion portion, and an insertion assisting device having a substantially tubular shape. The insertion assisting device includes an insertion path, a ventilation hole and a ventilation duct. The insertion portion of an endoscope is inserted into the insertion path. The ventilation hole is formed on a distal-end surface or outer circumferential surface of the insertion assisting device. The ventilation duct communicates with the ventilation hole and is different from the insertion path. The ventilation duct is connected to a suction device through a duct provided in the endoscope.

With the configuration of [9], sine the ventilation duct of the insertion assisting device is connected to the suction device through the duct, which is provided in the endoscope, the number of long tubes exposed to the outside can be decreased, as compared with the case where the ventilation duct of the insertion assisting device is directly connected to the suction device through a tube. Therefore, it is possible to enhance the operationality of the insertion assisting device.

[10] In the endoscope apparatus of [9], the duct, which is provided in the endoscope, may be inserted into an inside of a universal cable that extends from a hand operation unit of the endoscope, so as to be connected to another equipment.

With the configuration of [10], since the duct connected to the ventilation duct is disposed in the universal cable, the number of cables extending from the hand operation unit of the endoscope can be prevented from increasing. Therefore, it is possible to enhance the operationality of the endoscope.

[11] In the endoscope apparatus of [9], the duct, which is provided in the endoscope, may be a forceps channel through which suction is performed from a forceps port formed on a distal-end portion of the insertion portion. The ventilation duct of the insertion assisting device may communicate with the forceps channel.

With the configuration of [11], the forceps channel can be used to perform the suction from the ventilation duct of the insertion assisting device. Therefore, it is not necessary to provide new ducts in the endoscope or to provide a suction unit separately, which makes it possible to reduce a manufacturing cost of the endoscope apparatus.

[12] In the endoscope apparatus of any one of [9] to [11], an opening that communicates with a portion diverging from the ventilation duct may be formed in a grasp portion of the insertion assisting device. The ventilation duct may be opened to an outside through the opening.

With the configuration of [12], the ventilation duct is opened to the outside through the opening of the grasp portion. Therefore, even if a suction force is applied to the ventilation duct, the suction from the ventilation hole is not performed. Furthermore, when the opening of the grasp portion is closed, the ventilation duct is blocked from outside. Therefore, if a suction force is applied to the ventilation duct in this state, the suction from the ventilation hole can be performed. Accordingly, with the configuration of [12], when an operator grasps the grasp portion of the insertion assisting device and closes the opening or releases the closing, the operator can switch between the suction from the ventilation hole and the stop of the suction.

[13] In the endoscope apparatus of any one of [9] to [12], an inflatable balloon may be mounted on the outer circumference of the distal-end portion of the insertion assisting device.

With the configuration of [13], since the balloon is mounted on the outer circumference of the distal-end portion of the insertion assisting device, the distal-end portion of the insertion assisting device can be fixed to the inside of the body by inflating the balloon. Further, when the insertion assisting device is withdrawn while the balloon inflates, the air accumulated in the body can be discharged to the outside from the ventilation hole through the ventilation duct. Therefore, it is possible to smoothly withdraw the insertion assisting device.

According to the above-described insertion assisting device, since the liquid storage unit is provided, the liquid such as the body fluid flowing into the ventilation duct through the ventilation hole is stored in the liquid storage unit. Therefore, the liquid can be prevented from leaking and contaminating a working region.

Also, according to the above-described endoscope apparatus, since the ventilation duct of the insertion assisting device is connected to the suction device through the duct, which is provided in the endoscope apparatus, the number of long tubes exposed to the outside can be decreased as compared with the case where the ventilation duct of the insertion assisting device is directly connected to the suction device. Therefore, it is possible to enhance the operationality of the insertion assisting device.

DETAILED DESCRIPTION OF EMBODIMENTS OF THE INVENTION

Hereinafter, an insertion assisting device and an endoscope apparatus according to embodiments of the invention will be described with reference to the accompanying drawings.

Figure 1:
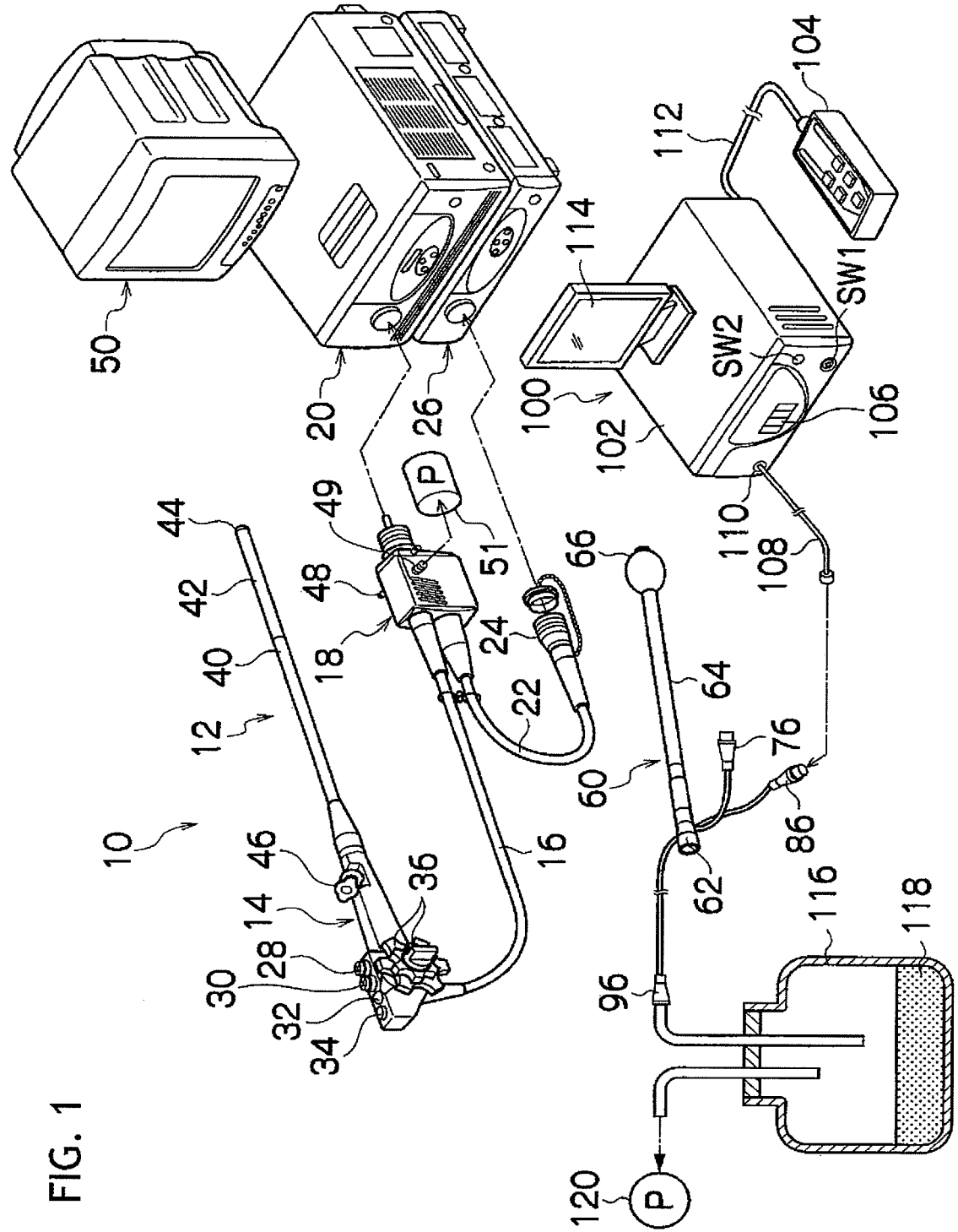
FIG. 1 is a diagram showing the system configuration of an endoscope apparatus that uses an insertion assisting device according to first and second embodiments of the invention.

FIG. 1 is a diagram showing the system configuration of an endoscope apparatus to which an insertion assisting device according to the invention is applied. As shown in FIG. 1, the endoscope apparatus mainly includes an endoscope 10, an insertion assisting device 60, and a balloon control device 100.

The endoscope 10 includes a hand operation unit 14 and an insertion portion 12 that is connected to the hand operation unit 14 and is inserted into the body. A universal cable 16 is connected to the hand operation unit 14, and an LG connector 18 is provided in the distal end of the universal cable 16. The LG connector 18 is detachably connected to a light source device 20, thereby transmitting illumination light to an illumination optical system 54 (see FIG. 2) which will be described below. Furthermore, the LG connector 18 is connected to an electric connector 24 through a cable 22, and the electric connector 24 is detachably connected to a processor 26.

The hand operation unit 14 has an air/water supply button 28, a suction button 30, a shutter button 32, and a function switching button 34, which are provided in parallel to each other. Furthermore, the hand operation unit 14 includes a pair of angle knobs 36 and 36.

The insertion portion 12 includes a flexible portion 40, a curved portion 42, and a distal-end portion 44 that are sequentially provided from the side of the hand operation unit 14. The curved portion 42 is remotely curved by rotating the angle knobs 36 and 36 of the hand operation unit 14. Accordingly, the distal-end portion 44 can be directed to a desired direction.

Figure 2:
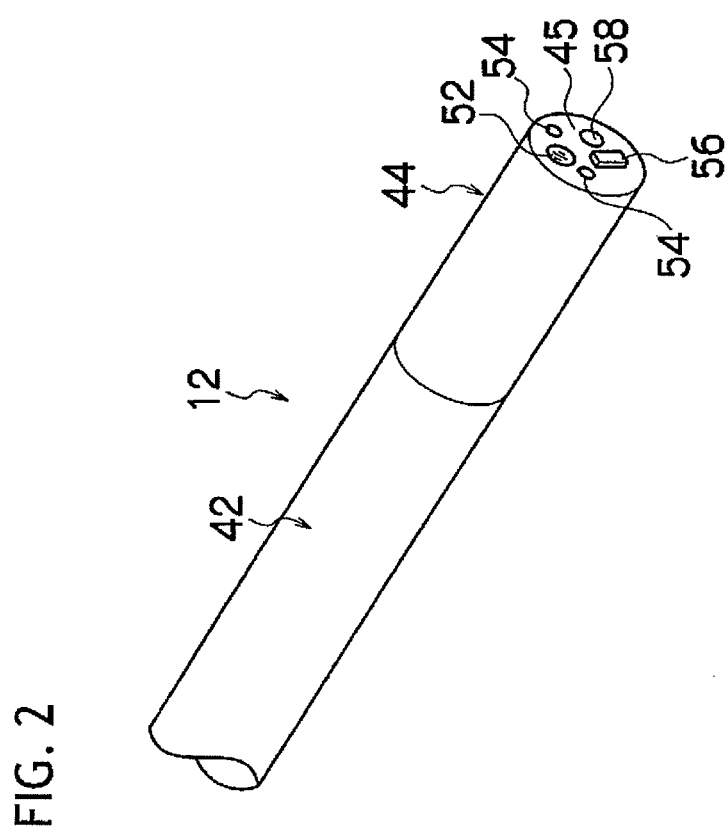
FIG. 2 is a perspective view showing a distal-end portion of an insertion portion of an endoscope.

As shown in FIG. 2, an observation optical system 52, a pair of illumination optical systems 54 and 54, an air/water supply nozzle 56, and a forceps port 58 are provided on the distal-end surface 45 of the distal-end portion 44. In the rear side of the observation optical system 52, a CCD (charge-coupled device) which is not shown is disposed. A signal cable (not shown) is connected to a substrate that supports the CCD. The signal cable is inserted into the insertion portion 12, the hand operation unit 14, and the universal cable 16 of FIG. 1 so as to extend to the electric connector 24 and is connected to the processor 26. Accordingly, an observed image captured by the observation optical system 52 is formed on the light receiving surface of the CCD so as to be converted into an electrical signal. Then, the electrical signal is output to the processor 26 through the signal cable so as to be converted into an image signal. Accordingly, the observed image is displayed on a monitor 50 connected to the processor 26.

In the rear side of the illumination optical systems 54 and 54 of FIG. 2, a light emitting end of a light guide (not shown) is disposed. The light guide is inserted into the insertion portion 12, the hand operation unit 14, and the universal cable 16 of FIG. 1 such that the light receiving end thereof is disposed within the LG connector 18. Therefore, as the LG connector 18 is connected to the light source device 20, illumination light irradiated from the light source device 20 is transmitted to the illumination optical systems 54 and 54 through the light guide and is then irradiated forward from the illumination optical systems 54 and 54.

The air/water supply nozzle 56 of FIG. 2 communicates with a valve (not sown) that is operated by the air/water supply button 28 of FIG. 1, and the valve communicates with an air/water supply connector 48 provided on the LG connector 18. The air/water supply connector 48 is connected to an air/water supply unit (not shown) that supplies air and water. Therefore, by operating the air/water supply button 28, air or water can be sprayed toward to the observation optical system 52 from the air/water nozzle 56.

The forceps port 58 of FIG. 2 communicates with a forceps insertion portion 46 of FIG. 1. Accordingly, as a treatment instrument such as forceps is inserted from the forceps insertion portion 46, the treatment instrument can be drawn from the forceps port 58. Furthermore, the forceps port 58 communicates with a valve (not shown) that is operated by the suction button 30, and the valve is connected to a suction connector 49 of the LG connector 18. Therefore, as a suction pump 51 is connected to the suction connector 49 and the valve is operated by the suction button 30, a lesion part or the like can be suctioned from the forceps port 58.

Meanwhile, the insertion assisting device 60 of FIG. 1 mainly includes a grasp portion 62 and a tube main body 64. The grasp portion 62 that is grasped by an operator is made of a rigid material such as plastic and is formed in a tubular shape. The tube main body 64 is fitted into the distal-end side of the grasp portion 62 so as to be fixed.

Figure 3:
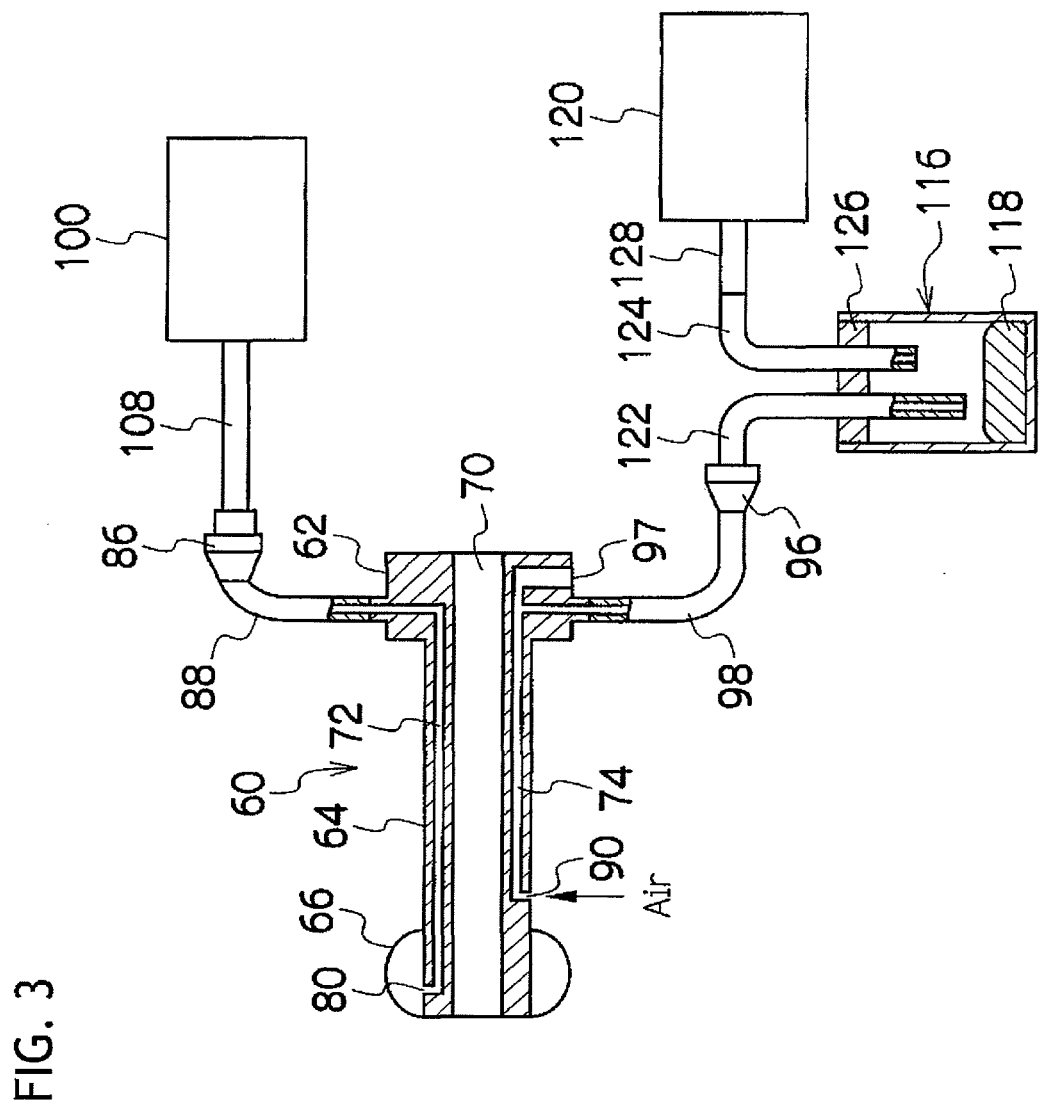
FIG. 3 is a diagram schematically showing the duct configuration of the inserting assisting device and surrounding equipments.
Figure 4:
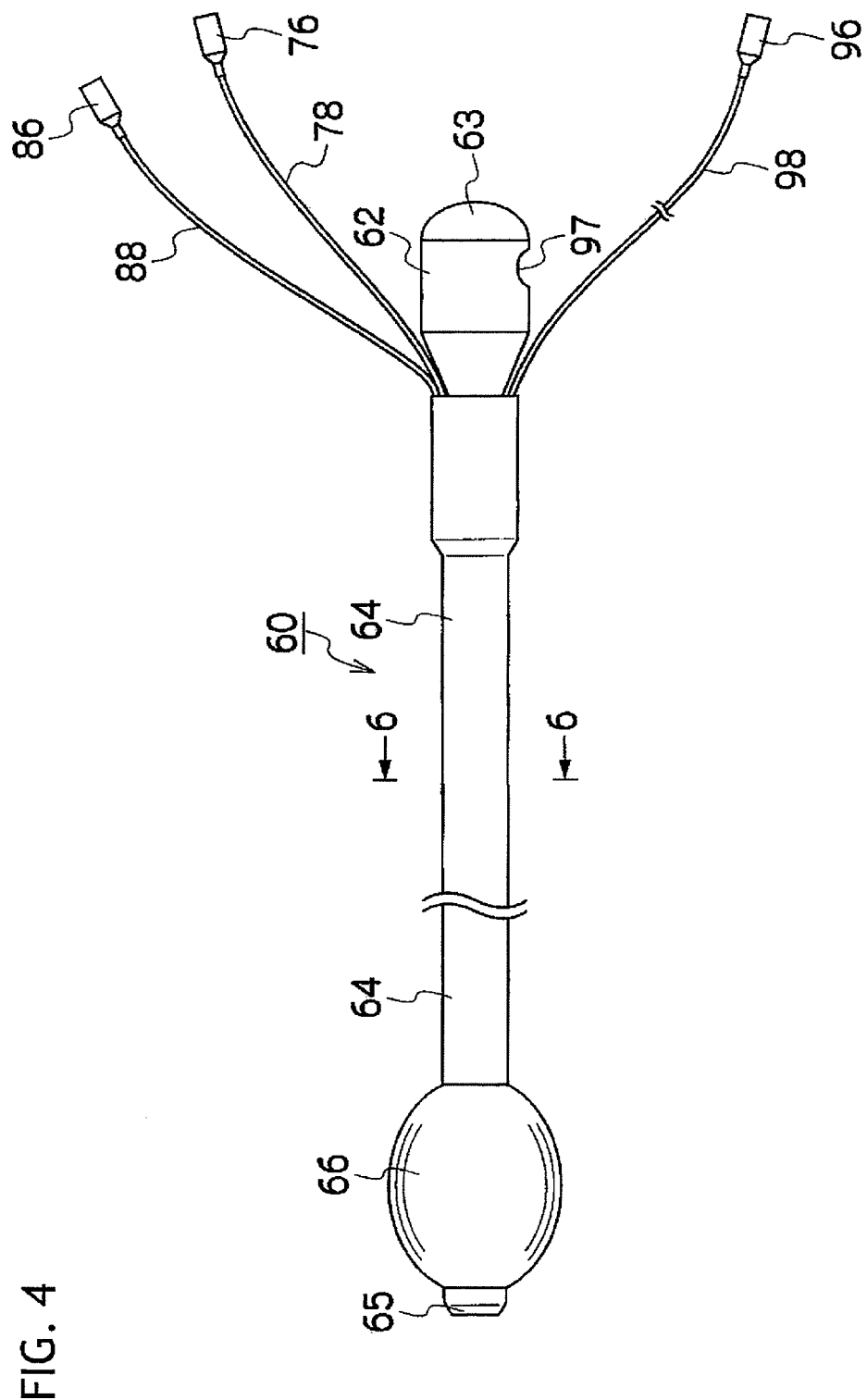
FIG. 4 is a front view of the insertion assisting device.
Figure 5:
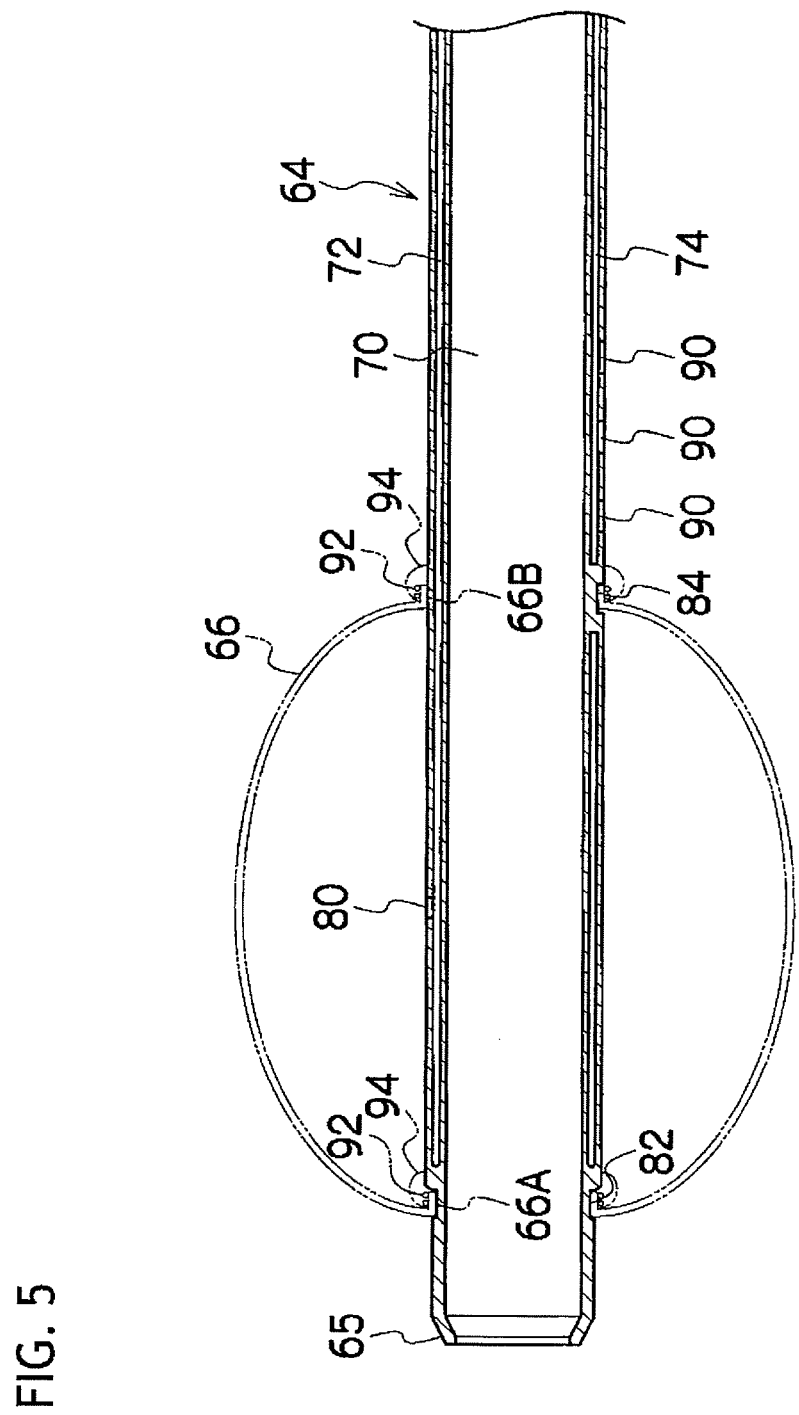
FIG. 5 is a section view of a distal-end portion of a tube main body.
Figure 6:
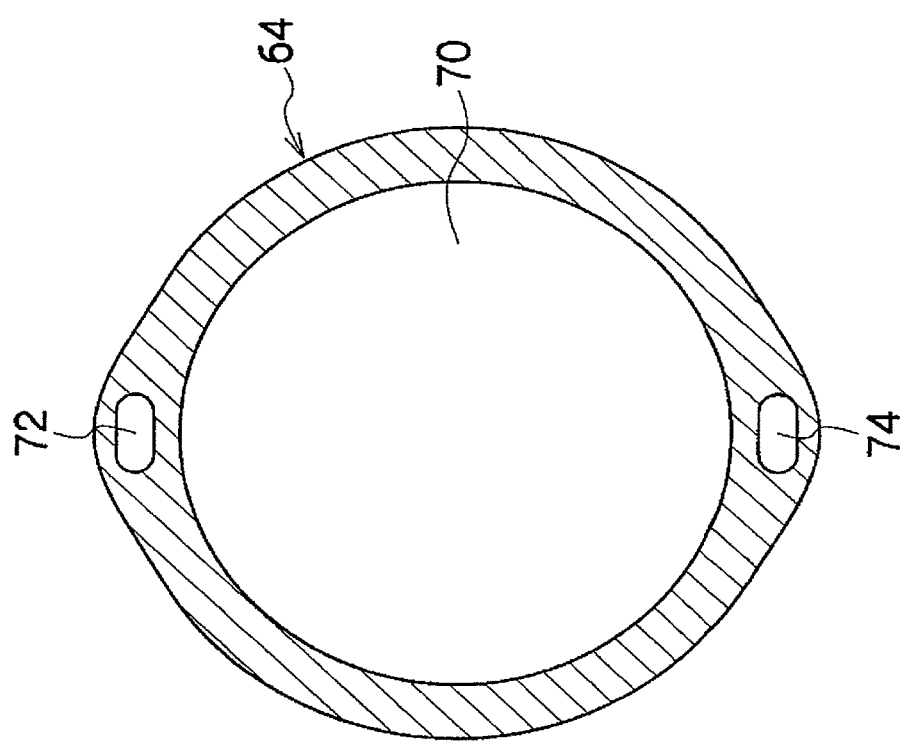
FIG. 6 is a section view taken along the line 6-6 of FIG. 4.

FIG. 3 is a diagram schematically showing the duct configuration of the inserting assisting device and surrounding equipments. FIG. 4 is a plan view of the insertion assisting device 60. FIG. 5 is a section view of the distal-end portion of the tube main body 64. FIG. 6 is a section view taken along a line 6-6 of FIG. 4.

The tube main body 64 made of a flexible material such as polyurethane is formed in a substantially tubular shape. As shown in FIGS. 5 and 6, the tube main body 64 includes an insertion path 70, a balloon fluid duct 72, and a ventilation duct 74, which are formed in an axial direction.

The insertion path 70 is a hole into which the insertion portion 12 (refer to FIG. 1) of the endoscope 10 is inserted. The section shape of the insertion path 70 taken along a surface perpendicular to the axial direction is circular, and the inner diameter of the insertion path 70 is slightly larger than the outer diameter of the insertion portion 12. The inner circumferential surface of the insertion path 70 is coated with a hydrophilic coating material (lubricant coating material) such as polyvinyl pyrrolidone. As a lubricant agent such as water is supplied onto the inner circumferential surface of the insertion path 70 (that is, a gap between the tube main body 64 and the insertion portion 12), it is possible to reduce the friction between the tube main body 64 and the insertion portion 12. Furthermore, the lubricant agent is injected from a connector 76 shown in FIG. 4 by an injector (not shown) or the like. The connector 76 is connected to a tube 78 having a small diameter, and the distal end of the tube 78 is connected to the base end of the insertion path 70. Therefore, the lubricant agent injected into the connector 76 by the injector or the like is supplied between the tube main body 64 and the insertion portion 12.

To prevent the supplied lubricant agent from leaking, a taper 65 is formed on the distal end of the tube main body 64 and is narrowed toward the distal end. Therefore, when the insertion portion 12 of the endoscope 10 is inserted into the insertion portion 70, the gap between the insertion portion 12 and the distal end of the tube main body 64 decreases, which makes it possible to prevent the lubricant agent from leaking into the distal-end side of the tube main body 64.

Furthermore, to prevent the lubricant agent from leaking, a tube 63 for preventing leakage is provided on the base end of the insertion assisting device 60 (that is, the base end of the grasp portion 62). The tube 63 for preventing leakage is made of an elastic material such as rubber, and is formed in such a manner that its diameter decreases toward the right side of FIG. 4. Therefore, the gap between the tube 63 and the insertion portion 12 decreases, which makes it possible to prevent the lubricant agent from leaking.

The balloon fluid duct 72 of FIG. 5 is a duct for supplying/suctioning fluid (for example, air) to and from a balloon 66 and is formed inside the tube wall of the insertion path 70 in the axial direction. Furthermore, as shown in FIG. 6, the balloon fluid duct 72 is formed in such a manner that the section shape of the balloon fluid duct 72 taken along a surface perpendicular to the axial direction of the tube main body 64 is an ellipse that is short in the diameter direction of the tube main body 64 and long in the circumferential direction of the tube main body 64. Therefore, while the flow-path area of the duct 72 is sufficiently secured, the tube main body 64 can be prevented from projecting to the outside. Furthermore, as long as the duct 72 has a section shape which is short in the diameter direction of the tube main body 64 and long in the circumferential direction of the tube main body 64, any section shape may be used. For example, the duct 72 may have a section shape being curved in parallel to the inner circumferential surface of the insertion path 70.

The distal-end side of the balloon fluid duct 72 is closed at the fixed position of the distal-end portion 66A of the balloon 66. Furthermore, the duct 72 communicates with a balloon opening 80 formed on the outer circumferential surface of the tube main body 64, and the opening 80 is formed in the mounting position (specifically, in the middle position of concave portions 82 and 84 which will be described below) of the balloon 66. As the air is supplied to and suctioned from the opening 80, the balloon 66 inflates and deflates.

The tube 88 of FIG. 4 is connected to the base-end side of the duct 72, and a connector 86 is provided on the end portion of the tube 88. As a tube 108 of FIG. 1 is connected to the connector 86, the balloon fluid duct 72 is connected to the balloon control device 100. Therefore, as the balloon control device 100 supplies and suctions the air, the balloon 66 can be inflated and deflated.

As shown in FIG. 6, the ventilation duct 74 is provided in the opposite side to the balloon fluid duct 72 with the insertion path 70 being interposed therebetween, and is formed within the tube wall of the insertion path 70 in the axial direction. Similar to the balloon fluid duct 72, the ventilation duct 74 has an elliptical section shape that is short in the diameter direction and long in the circumferential direction, as shown in FIG. 6. Therefore, while a flow path area of the duct 74 is sufficiently secured, it is possible to prevent the tube main body 64 from projecting outside. Furthermore, as long as the duct 74 has a section shape which is short in the diameter direction and long in the circumferential direction, any section shape may be used. For example, the duct 74 may have a section shape being curved in parallel to the inner circumferential surface of the insertion path 70.

As shown in FIG. 5, the distal-end side of the ventilation duct 74 is closed at the fixed position of a base-end portion 66B of the balloon 66. Furthermore, the duct 74 communicates with the outside through ventilation openings 90, 90, and 90 (corresponding to ventilation holes) formed on the outer circumferential surface of the tube main body 64. The ventilation openings 90, 90, and 90 are formed at even intervals to be closer to the base-end side than the mounting position of the balloon 66. The respective openings 90 are formed to be larger than the section area of the duct 74. Thereby, even with only one opening 90, sufficient ventilation can be achieved.

As shown in FIG. 3, the base-end side of the duct 74 diverges so as to communicate with an opening 97 formed in the grasp portion 62. The opening 97 is formed in such a size and shape as to be closed by the finger of an operator. For example, the opening 97 may be formed in a circular or elliptical shape. Therefore, as the operator closes the opening 97 with his/her finger while grasping the grasp portion 62, the duct 74 can be blocked from the outside. Furthermore, if the operator stops to close the opening 97, the duct 74 can be opened to the outside.

The base-end side of the duct 74 communicates with a connector 96 through a tube 98, and the connector 96 is connected to the upper end portion of a pipe 122 of a liquid reservoir tank 116. The pipe 122 is dispersed so as to pass through a lid 126 of the liquid reservoir tank 116, and the lower end of the pipe 122 is disposed in the liquid reservoir tank 116 so as to be separated from the bottom surface of the liquid reservoir tank 116. Accordingly, liquid flowing out of the duct 74 is stored in the liquid reservoir tank 116.

Inside the liquid reservoir tank 116, a sponge 118 serving as a liquid holding unit is provided. Therefore, the liquid stored in the liquid reservoir tank 116 can be absorbed by the sponge 118 so as to be held. For example, even if the liquid reservoir tank 116 is laterally turned, the liquid can be prevented from leaking to the outside. Furthermore, the liquid holding unit is not limited to the sponge 118, but may be an absorbent sheet which absorbs liquid or a polymer which gelatinizes or solidifies liquid. Furthermore, the liquid holding unit may be omitted.

The liquid reservoir tank 116 has a pipe 124 serving as a discharge path. Similar to the pipe 122, the pipe 124 is disposed so as to pass through the lid 126, and the lower end thereof is disposed in the liquid reservoir tank 116 so a to be separated from the bottom surface of the liquid reservoir tank 116. Therefore, a fluid mixture of gas and liquid flowing out of the duct 74 is processed in such a manner that only the liquid is stored in the liquid reservoir tank 116 and the gas is discharged from the pipe 124. Preferably, the lower end of the pipe 124 is disposed above the lower end of the pipe 122 so as to reliably prevent liquid from flowing into a suction pump 120 which will be described below.

The upper end of the pipe 124 is connected to the suction pump 120 through a tube 128. Thereby, the openings 90 of the tube main body 64 are connected to the suction pump 120 through the duct 74, the tube 98, the pipe 122, the liquid reservoir tank 116, the pipe 124, and the tube 128. Accordingly, as the suction pump 120 is driven, it is possible to perform suction from the openings 90. At this time, when liquid such as body fluid is suctioned from the openings 90, the liquid is stored in the liquid reservoir tank 116, and only the gas is suctioned into the suction pump 120.

As shown in FIG. 5, the tube main body 64 has two concave portions 82 and 84 formed on the outer circumference thereof in the mounting positions of the balloon 66, with the concave portions 82 and 84 being spaced at a predetermined distance. The distal-end side concave portion 82 is formed along the entire outer circumference of the tube main body 64. The base-end side concave portion 84 is formed in a C shape such that the surrounding of the balloon fluid duct 72 is excluded. The distal-end portion 66A and the base-end portions 66B of the balloon 66 are fixed to the concave portions 82 and 84, respectively.

The balloon 66 is formed in a substantially tubular shape so that its central portion is inflatable. In a state where the balloon 66 is set inside out, the distal-end portion 66A thereof is put on the concave portion 82 of the tube main body 64. Then, a thread 92 is wound around the distal-end portion 66A of the balloon 66, and an adhesive 94 is applied to the thread 92 such that the distal-end portion 66A of the balloon 66 is fixed to the tube main body 64. In this state, the balloon 66 is returned to the original state, and the base-end portion 66B of the balloon 66 is put on the concave portion 84. Then, a thread 92 is wound around the base-end portion 66B of the balloon 66, and the adhesive 94 is applied to the thread 92 such that the base-end portion 66B of the balloon 66 is fixed to the tube main body 64. Accordingly, the distal-end portion 66A and the base-end portion 66B of the balloon 66 are fixed to the concave portions 82 and 84, respectively. At this time, since the distal-end portion 66A and the base-end portion 66B of the balloon 66 are disposed in the concave portions 82 and 84, respectively, the fixed portions can be prevented from projecting outwardly.

The tube main body 64 is manufactured by processing a multilumen tube having a constant section shape. The multilumen tube before the processing is not illustrated, but three holes composed of the insertion path 70, the duct 72 (corresponding to the insertion path), and the duct 74 (corresponding to the ventilation duct) are formed to pass through the processed multilumen tube in the axial direction thereof. The cross-section of the multilumen tube perpendicular to its axis is formed in a uniform shape at all times. A cored bar is inserted into the multilumen tube, a tubular pressing die having two convex portions formed on the inner circumferential surface thereof is pressed against the multilumen tube from outside, and the multilumen tube is heated at a predetermined temperature (for example, 100-110° C.). Then, the tube main body 64 having the two concave portions 82 and 84 is manufactured.

The balloon control device 100 of FIG. 1 serves to supply and suction fluid such as air to and from the balloon 66 and mainly includes a device main body 102 and a hand switch 104 for remote control.

On the front surface of the device main body 102, a power switch SW1, a stop switch SW2, and a pressure display section 106 are provided. The pressure display section 106 is a panel for displaying the pressure value of the balloon 66. When abnormalities occur in the balloon, for example, when the balloon is broken, a corresponding error code is displayed on the pressure display section 106.

A tube 108 for supplying and suctioning air to and from the balloon 66 is connected to the front surface of the device main body 102. In the connection portion between the tube 108 and the device main body 102, a backflow prevention unit 110 is provided. The backflow prevention unit 110 is constructed by assembling a gas/liquid separating filter into a hollow disk-shaped case (not shown) which is detachably mounted on the device main body 102. When the balloon 66 is broken, the filter can prevent liquid such as body fluid from flowing into the device main body 102.

The hand switch 104 has a variety of switches provided thereon. For example, a stop switch having the same function as the stop switch SW2 of the device main body 102, an on/off switch for instructing pressurization and depressurization of the balloon 66, and a pause switch for holding the pressure of the balloon 66 are provided. The hand switch 104 is electrically connected to the device main body 102 through a cord 112. Although not shown in FIG. 1, the hand switch 104 has a display section that displays an air-supply state or an air-discharge state of the balloon 66.

The balloon control device 100 configured in such a manner can supply air to the balloon 66 such that the balloon 66 inflates, and can control the air pressure to a constant value such that the balloon 66 is held in a inflating state. Also, the balloon control device 100 can suction the air from the balloon 66 such that the balloon 66 deflates, and can control the air pressure to a constant value such that the balloon 66 is held in a deflating state.

The balloon control device 100 is connected to a balloon monitor 114. When the balloon 66 inflates or deflates, the balloon control device 100 can display the pressure value or the inflating/deflating state of the balloon 66 on the balloon monitor 114. Also, the pressure value or the inflating/deflating state of the balloon 66 may be displayed on the monitor 50 with being superimposed on an observed image of the endoscope 10.

Now, an operation method of the endoscope apparatus configured in the above-described manner will be described. First, the insertion portion 12 and the insertion assisting device 60 are alternately inserted by a pushing manner, and the insertion assisting device 60 is fixed in the body (for example, the large intestine) by inflating the balloon 66, if necessary. Also, the insertion assisting device 60 is moved in a withdrawal direction such that the tubular shape of the inside of the body (for example, the large intestine) is simplified. Then, the insertion portion 12 is further inserted into a deeper portion. For example, the insertion portion 12 is inserted from the anus of a patient, and when the distal end of the insertion portion 12 passes through the S-shaped colon, the insertion assisting device 60 is fixed to the intestine by inflating the balloon 66. Then, the insertion assisting device 60 is pulled so that the S-shape colon is set in a substantially straight-line shape. Also, the distal end of the insertion portion 12 is inserted into the deep potion of the intestine. Thereby, the insertion portion 12 can be inserted into the deep portion of the intestine.

However, among the above-described operations, in the operation for moving the insertion assisting device 60 in the withdrawal direction in a state where the balloon 66 inflates, the air accumulated between the tube main body 64 and the intestine wall can be suctioned into the ventilation openings 90, 90, and 90 of the tube main body 64. That is, since the ventilation openings 90 are connected to the suction pump 120 through the duct 74 within the tube main body 64, the tube 98, the pipe 122, the liquid reservoir tank 116, the pipe 124, and the tube 128, the air can be suctioned into the openings 90 by driving the suction pump 120. Therefore, when the insertion assisting device 60 is operated in the withdrawal direction, the air accumulated between the tube main body 64 and the intestine wall is suctioned. Accordingly, the compression can be prevented, and the insertion assisting device 60 can be smoothly operated in the withdrawal direction. Furthermore, when the suction from the ventilation openings 90 to begin, an operator closes the opening 97 of the grasp portion 62 by his/her finger. When the suction operation is to be stopped, the operator removes the finger from the opening 97 of the grasp portion 62 so as to stop the closing.

According to this embodiment, since the air can be suctioned from the ventilation openings 90, the withdrawal operation of the insertion assisting device 60 can be performed smoothly. Furthermore, the liquid reservoir tank 116 is provided on the duct through which the openings 90 and the suction pump 120 are connected to each other. Therefore, when liquid such as body fluid is suctioned from the openings 90, the liquid can be stored in the liquid reservoir tank 116. As a result, the body fluid flowing out of the duct 74 can be prevented from leaking and contaminating a working region.

According to this embodiment, since the opening 97 is provided in the grasp portion 62, the suction operation can be simply started or stopped by closing the opening 97 or releasing the closing.

According to the first embodiment, the on/off operation of suction is switched by closing the opening 97 of the grasp portion 62. However, instead of the opening 97, an opening and closing valve may be provided in the duct 74 such that the duct 74 is opened to the atmosphere or is blocked from the atmosphere by opening or closing valve.

Figure 7:
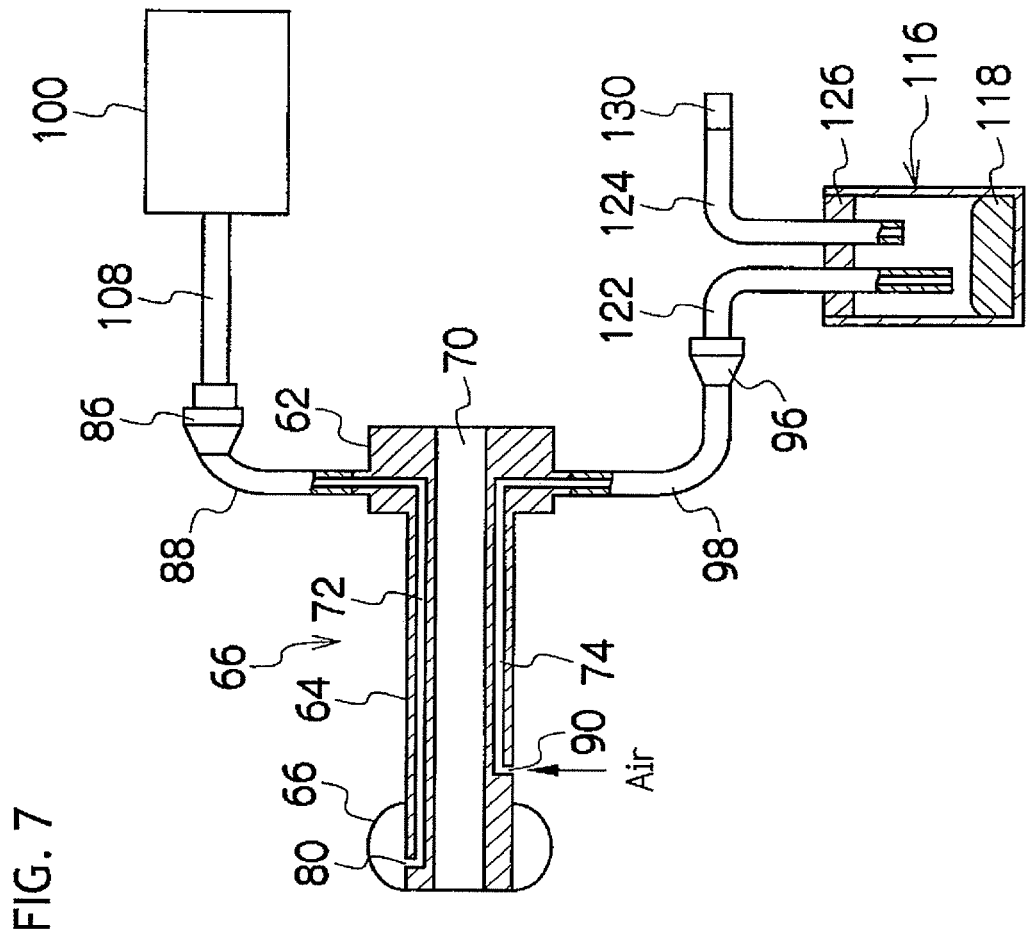
FIG. 7 is a diagram schematically showing the duct configuration of the insertion assisting device according to the second embodiment of the invention.

Next, a second embodiment of the invention will be described. FIG. 7 is a diagram schematically showing the duct configuration of the second embodiment. The second embodiment shown in FIG. 7 is different from the first embodiment shown in FIG. 3 in that the opening 97 of the grasp portion 62 and the suction pump 120 in the first embodiment are not provided, and that a check valve 130 is provided in the pipe 124.

Figure 8A:
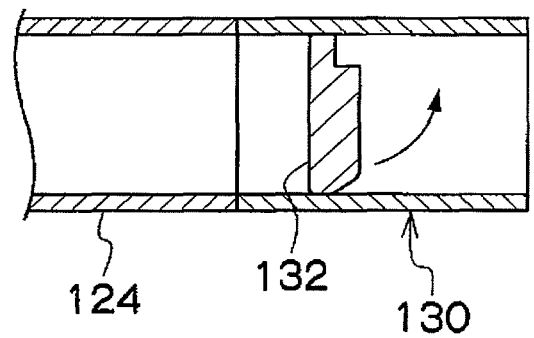
FIGS. 8A and 8B are section views of a check valve.
Figure 8B:
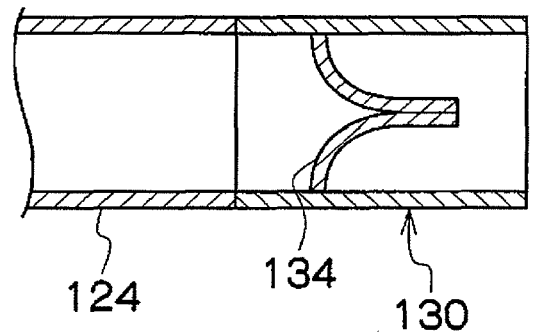

The check valve 130 is a member for preventing gas from flowing into the pipe 124 from the outside (that is, a gas flow from the base end to the distal end within the duct 74). FIGS. 8A and 8B show the configuration of the check valve 130. The check valve 130 of FIG. 8A has a closing member 132 which swings only toward the outside (the arrow direction of FIG. 8A). Only when gas flows out of the pipe 124, the closing member 132 swings. The check valve 130 of FIG. 8B has a throttle 134 that is gradually narrowed toward the outside so as to close. Only when gas flows out of the duct 74, the throttle 134 opens to discharge the gas.

In the second embodiment configured in such a manner, when the pressure in the vicinity of the openings 90 increases, the air surrounding the openings 90 is naturally discharged to the outside through the openings 90, the duct 74, the tube 98, the pipe 122, the liquid reservoir tank 116, and the pipe 124. At this time, since liquid such as body fluid flowing from the openings 90 is stored in the liquid reservoir tank 116, it is possible to prevent the liquid from leaking and contaminating a working region.

Also, in the second embodiment, the check valve 130 is provided. Therefore, even when the pressure in the vicinity of the openings 90 decreases, the liquid within the duct 74 can be prevented from flowing backward into the body from the openings 90.

In the second embodiment, the position of the check valve 130 is not limited to the pipe 124, but may be provided in any position of the flow path communicating with the duct 74. Furthermore, without the pipe 124 being provided, a hole passing through the lid 126 in the up and down direction may be formed in such manner that the check valve is provided in the hole.

In the first and second embodiments, it has been described that the liquid reservoir tank 116 is provided as a liquid storage unit. However, another liquid storage unit may be used so long as it can store liquid. For example, a liquid storage unit formed in a bag shape may be used.

Figure 9:
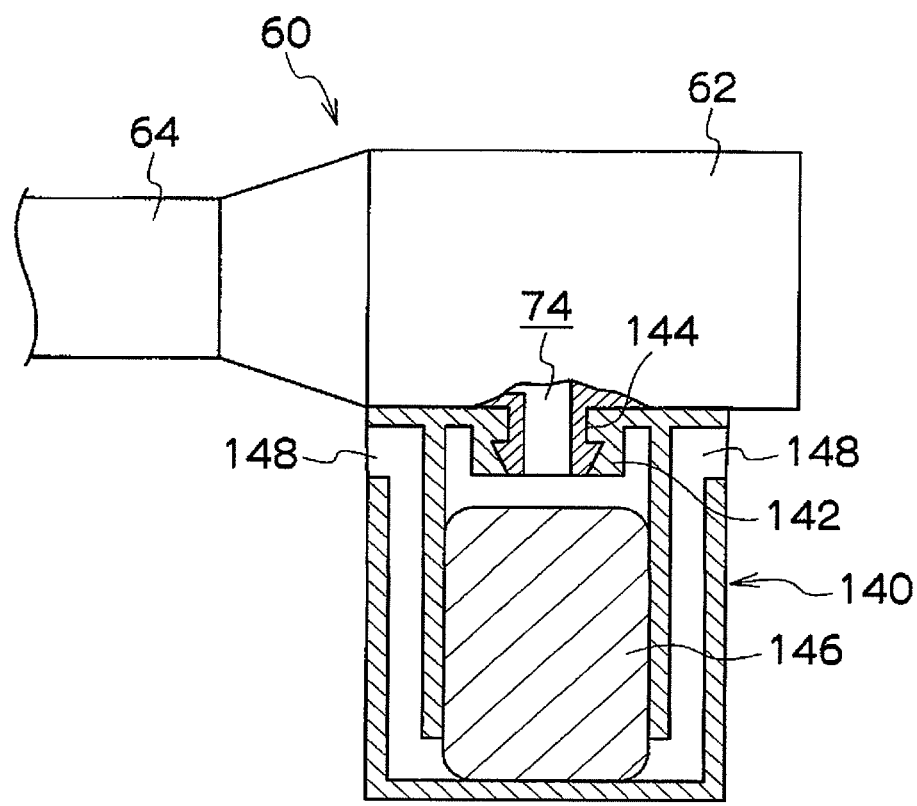
FIG. 9 is a section view of a detachable liquid reservoir unit.

In the above-described embodiments, the liquid storage unit (the liquid reservoir tank 116) is disposed separately from the insertion assisting device 60. However, the liquid storage unit may be directly attached to the grasp portion 62 of the insertion assisting device 60. For example, a liquid reservoir unit 140 shown in FIG. 9 has a mounting portion 142, and the mounting portion 142 is detachably fitted into a connector 144 of the grasp portion 62 of the insertion assisting device 60. As the mounting portion 142 is mounted on the connector 144, the duct 74 communicates with the inside of the liquid reservoir unit 140. Inside the liquid reservoir unit 140, an absorbent sheet 146 is provided, and liquid discharged into the liquid reservoir unit 140 is absorbed into the absorbent sheet 146. The liquid reservoir unit 140 has a gas-discharge port 148 in the upper portion thereof, and gas discharged into the liquid reservoir unit 140 is discharged from the gas-discharge port 148. Furthermore, a casing of the liquid reservoir unit 140 may be made of a rigid material such as plastic or a soft material such as vinyl and may be formed in a bag shape. Since the liquid reservoir unit 140 configured in such a manner can collect the liquid discharged from the duct 74, it is possible to prevent the liquid from leaking and contaminating a working region.

Figure 10:
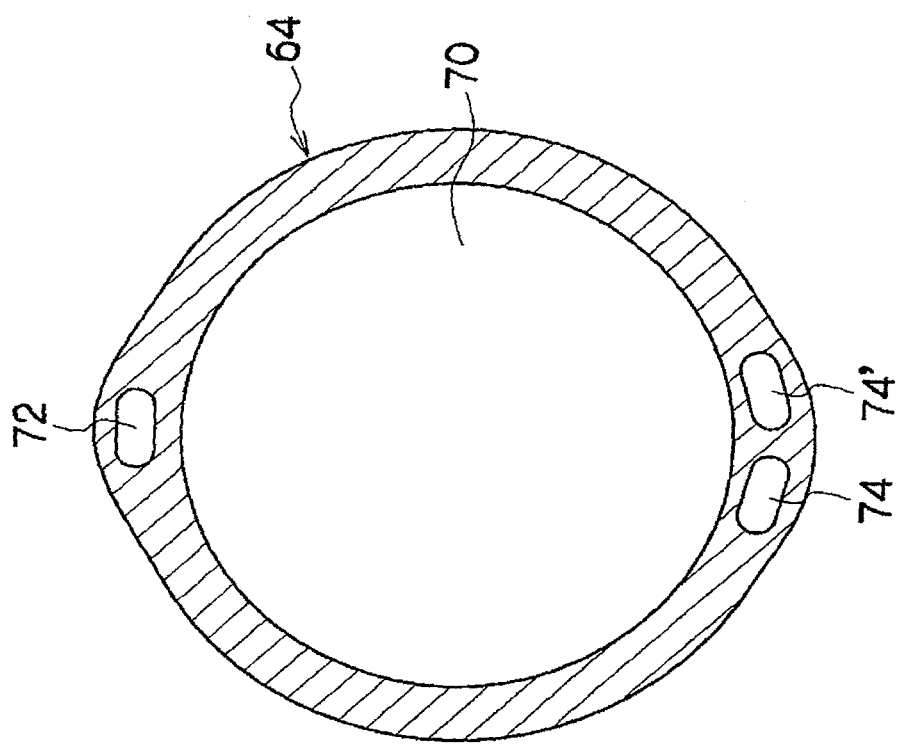
FIG. 10 is a section view of a tube main body that is different from one shown in FIG. 6.

In the first and second embodiments, the ventilation holes (openings 90) are formed on the outer circumferential surface of the tube main body 64. However, a ventilation hole may be formed on the distal-end surface of the tube main body 64. Also, the ventilation hole may be formed on both of the outer circumferential surface and the distal-end surface of the tube main body 64. In this case, as shown in FIG. 10, a duct 74' communicating with the opening (not shown) of the distal-end surface is provided separately from the duct 74 communicating with the openings 90 of the outer circumferential surface. The duct 74' may be disposed in the opposite side to the duct 72 and in the vicinity of the duct 74.

The above-described embodiments are examples of a single-balloon endoscope apparatus in which the balloon 66 is mounted on only the insertion assisting device 60. However, another balloon which can inflate and deflate may be mounted on the insertion portion 12 of the endoscope 10 such that the endoscope apparatus is used as a double-balloon endoscope apparatus. In this case, the distal end of the insertion portion 12 can be inserted into a deep portion of the intestine by repeatedly performing the following operations: an insertion operation for inserting the insertion portion 12 of the endoscope 10, a fixing operation for fixing the insertion portion 12 by inflating the balloon of the insertion portion 12, a pushing operation for pushing the insertion assisting device 60 along the insertion portion 12, a grasping operation for grasping the intestine by inflating the balloon 66, and a hauling operation for hauling the insertion assisting device 60.

Next, an endoscope apparatus according to a third embodiment of the invention will be described. Similar reference numerals and terms will be attached to the same components as those of the first and second embodiments, and the duplicate descriptions thereon will be omitted.

Figure 11:
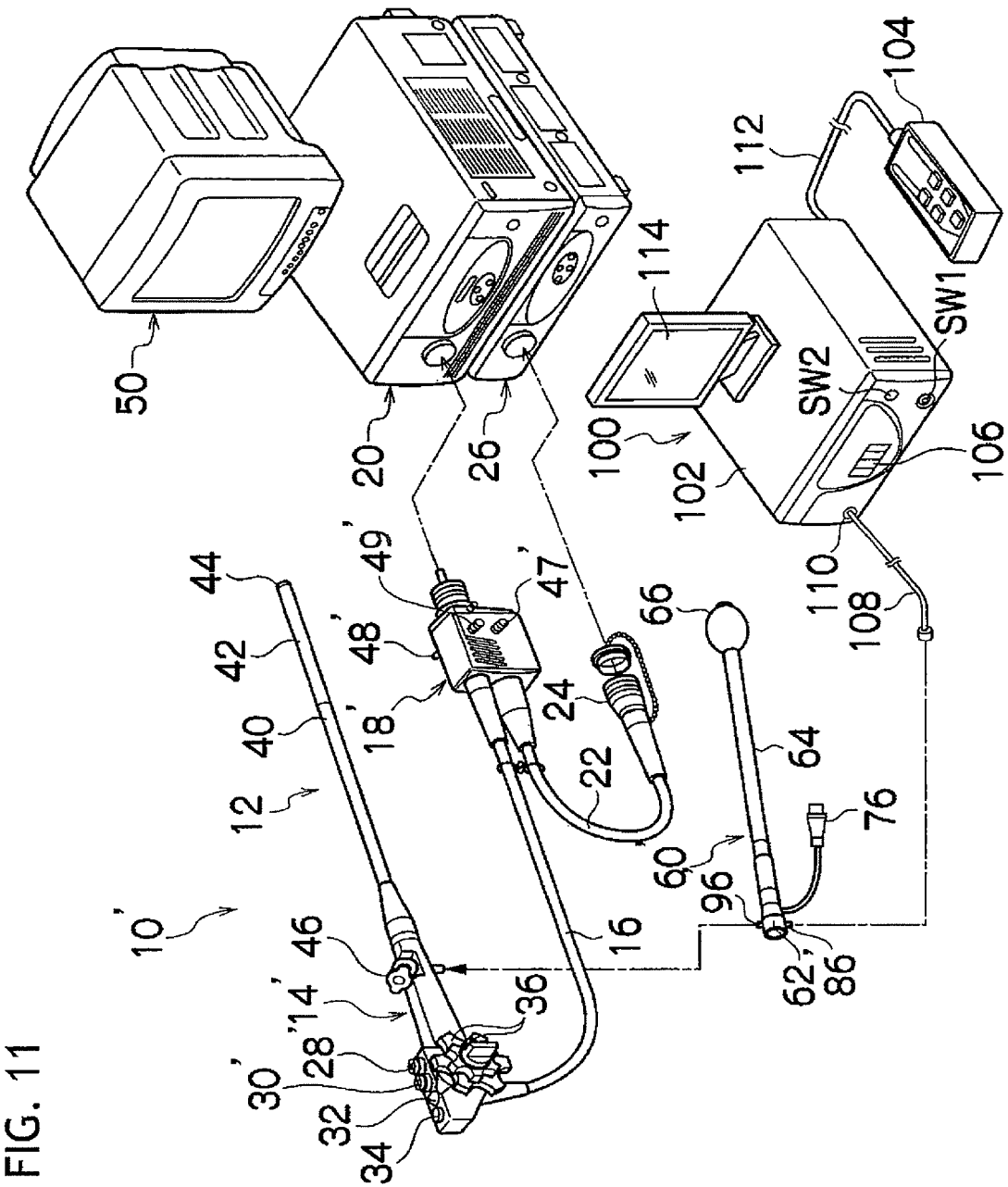
FIG. 11 is a diagram showing the system configuration of an endoscope apparatus according to third and fourth embodiments of the invention.

FIG. 11 is a diagram showing the system configuration of the endoscope apparatus according to the third embodiment of the invention. As shown in FIG. 11, the endoscope apparatus mainly includes an endoscope 10', an insertion assisting device 60', and a balloon control device 100.

As shown in FIG. 2, the observation optical system 52, the pair of illumination optical systems 54 and 54, the air/water supply nozzle 56, and the forceps port 58 are provided on the distal-end surface 45 of the distal-end portion 44.

Figure 12:
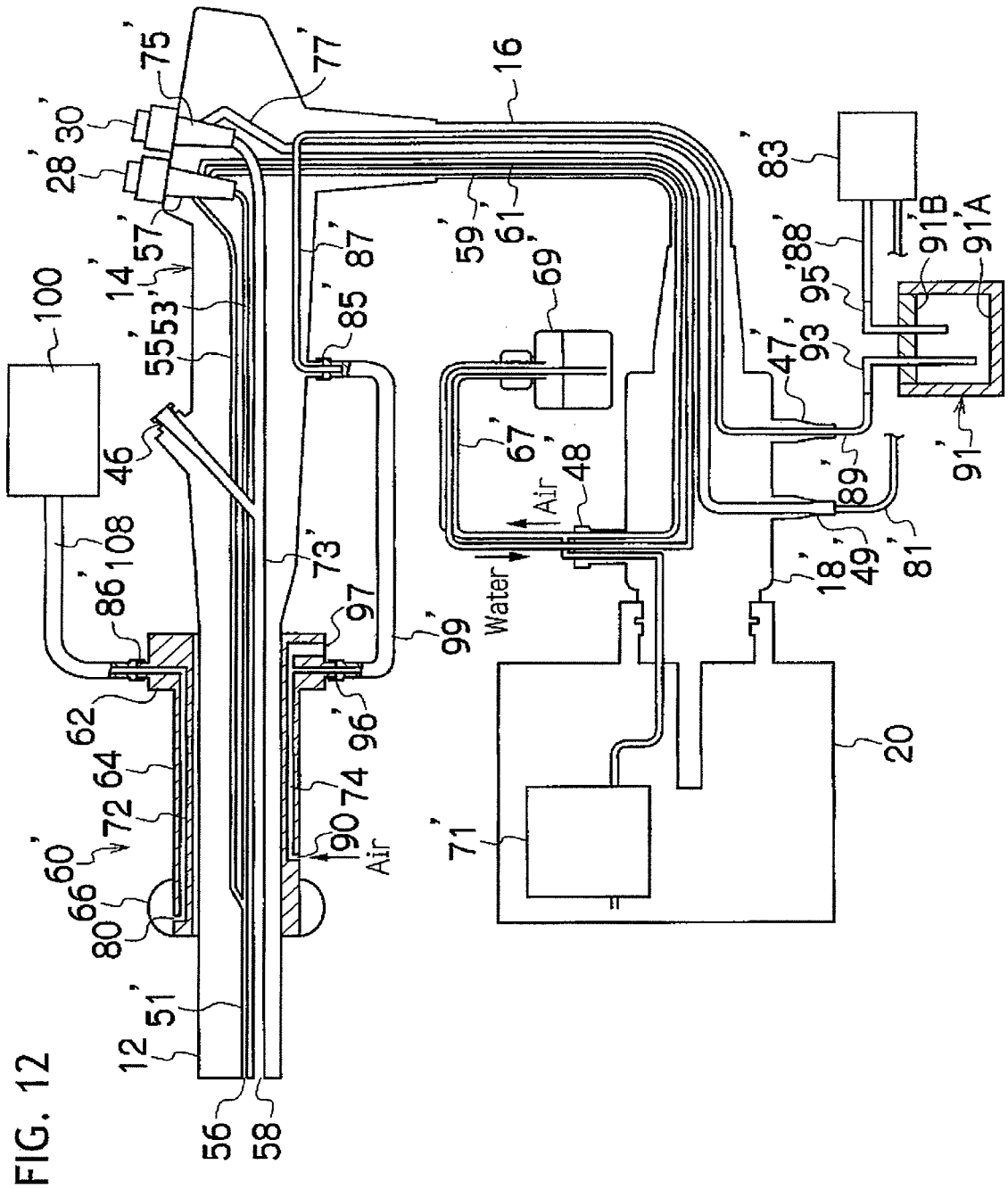
FIG. 12 is a diagram showing the duct configuration of the endoscope apparatus according to the third embodiment of the invention.

As shown in FIG. 12, the air/water supply nozzle 56 is connected to an air/water supply tube 51'. The air/water supply tube 51' diverges into an air supply tube 53' and a water supply tube 55' such that the air supply tube 53' and the water supply tube 55' are connected to a valve 57' disposed in the hand operation unit 14. The valve 57' is connected to an air feed tube 59' and a water feed tube 61' and has an air/water supply button 28' attached thereto. In a state where the air/water supply button 28' projects, the air supply tube 53' and the air feed tube 59' communicate with each other. As the air/water supply button 28' is pressed down, the water supply tube 55' and the water feed tube 61' communicate with each other. The air/water supply button 28' has a ventilation hole (not shown) formed therein such that the air feed tube 59' communicates with the external air through the ventilation hole. Therefore, as an operator closes the ventilation hole, the air fed from the air feed tube 59' is supplied to the air supply tube 53'.

The air feed tube 59' and the water feed tube 61' communicates with the inside of a universal cable 16' so as to extend to a water supply connector 48' of an LG connector 18'. A tube 67' is detachably connected to the water supply connector 48', and an end portion of the tube 67' is connected to a water storage tank 69'. Accordingly, the water feed tube 61' communicates with the lower portion of the water storage tank 69' than a liquid surface, and the air feed tube 59' communicates with the upper portion of the water storage tank 69' than the liquid surface. Furthermore, the air feed tube 59' diverges in an intermediate portion. When the LG connector 18' is connected to a light source device 20', a diverging part of the air feed tube 59' is connected to an air pump 71' within the light source device 20'. Therefore, as the air pump 71' is driven to supply air, the air is supplied to the air feed tube 59'. The air escapes to the outside through the ventilation hole (not shown) of the air/water supply button 28' when the air/water supply button 28' is not operated. Also, as an operator closes the ventilation hole, the air of the air feed tube 59' is supplied to the air supply tube 53' so as to be sprayed from the air/water supply nozzle 56. Furthermore, as the air/water supply button 28' is pressed down, the air feed tube 59' and the air supply tube 53' are blocked from each other. Therefore, the air fed to the air feed tube 59' is supplied onto the liquid surface of the water storage tank 69'. Accordingly, the internal pressure of the water storage tank 69' increases so that water is supplied to the water feed tube 61'. Then, the water is sprayed from the air/water supply nozzle 56' through the water supply tube 55'. As such, as the water or air is sprayed from the air/water supply nozzle 56, the water or air is blown against the observation optical system 52 such that the observation optical system 52 is washed.

The forceps port 58 is connected to a forceps tube 73' shown in FIG. 12. The forceps tube 73' diverges so as to communicate with the forceps insertion portion 46 and a valve 75'. Accordingly, as a treatment instrument (not shown) such as forceps is inserted from the forceps insertion portion 46, the treatment instrument can be drawn out of the forceps port 58. The valve 75' is connected to a suction tube 77' and has a suction button 30' attached thereto. In a state where the suction button 30' projects, the suction tube 77' communicates with the external air. As the suction button 30' is pressed down, the suction tube 77' and the forceps tube 73' are connected to each other. The suction tube 77' extends to a suction connector 49' of the LG connector 18' and communicates with a suction device 83' by connecting a tube 81' to the suction connector 49'. Therefore, as the suction button 30' is pressed down in a state where the suction device 83' is driven, a lesion part or the like can be suctioned from the forceps port 58.

Figure 13:
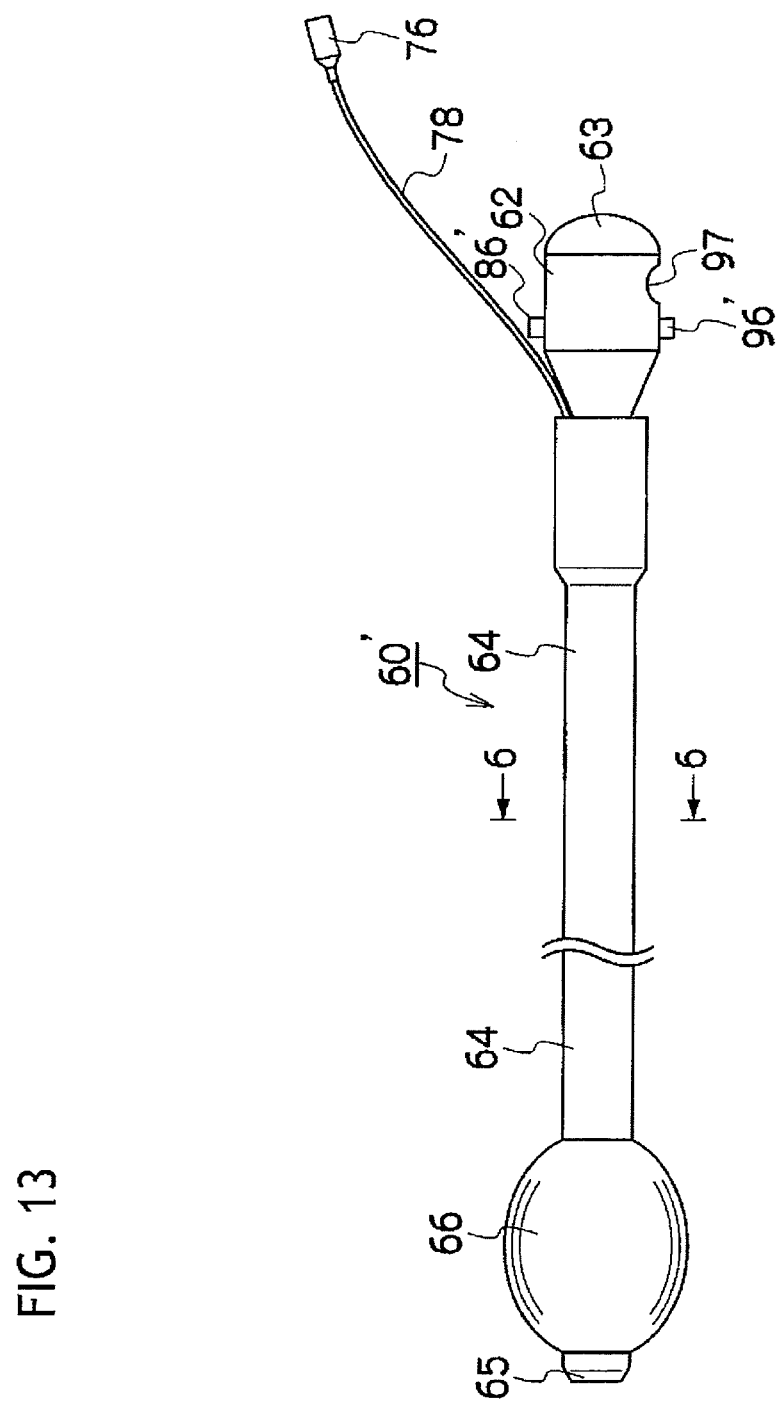
FIG. 13 is a front view of an insertion assisting device.

FIG. 13 is a plan view of the insertion assisting device 60'. A section view of the distal-end portion of the tube main body 64 according to the third embodiment is the same as the section view shown in FIG. 5. Furthermore, a section view taken along a line 6-6 of FIG. 13 is the same as the section view shown in FIG. 6.

The base-end side of the duct 72 communicates with a connector 86' of the grasp portion 62 shown in FIG. 12. As the tube 108 of FIG. 11 is connected to the connector 86', the balloon fluid duct 72 is connected to the balloon control device 100. Therefore, as the balloon control device 100 supplies and suctions air, the balloon 66 can be inflated and deflated. Also, as shown in FIG. 3, the tube 88 having the small diameter may be connected to the base-end side of the duct 72 such that the connector 86' is provided on the end portion of the tube 88.

The base-end side of the duct 74 communicates with a connector 96' provided in the grasp portion 62. The connector 96' is detachably connected to a connector 85' provided in the hand operation unit 14' of the endoscope 10' through a tube 99'. The tube 98 having the small diameter may be connected to the base-end side of the duct 74, the connector 96 may be provided on the end portion of the tube 98, and the connector 96 may be connected to the connector 85' of the hand operation unit 14'.

The connector 85' of the hand operation unit 14' is connected to a suction tube 87' (corresponding to a duct provided within the endoscope), and the suction tube 87' is inserted into the universal cable 16 so as to extend to a suction connector 47' of the LG connector 18'. The suction connector 47' is connected to a pipe 93' of a liquid reservoir tank 91' through a tube 89'. The pipe 93' is opened in the vicinity of a tank bottom surface 91'A inside the liquid reservoir tank 91'. Furthermore, a pipe 95' is connected to a lid 91'B of the liquid reservoir tank 91', and the suction device 83' is connected to the pipe 95' through a tube 88'. Accordingly, since the ventilation holes 90 are connected to the suction device 83', the suction from the ventilation holes 90 can be performed. At this time, when liquid such as body fluid is suctioned, the liquid is collected into the liquid reservoir tank 91', because the liquid reservoir tank 91' is disposed in the middle of the path.

In an operation for moving the insertion assisting device 60' in the withdrawal direction in a state where the balloon 66 inflates, the air accumulated between the tube main body 64 and the intestine wall can be suctioned from the ventilation openings 90, 90, and 90 of the tube main body 64. That is, the ventilation openings 90 communicate with the suction device 83' through the duct 74 and the tube 99' being provided within the tube main body 64 and the suction tube 87' and the tube 89', which are provided within the endoscope 10'. As an operator closes the opening 97 of the grasp portion 62 by his/her finger, the duct 74 is blocked from the outside, and the air is suctioned from the ventilation openings 90. Therefore, when the insertion assisting device 60' is operated in the withdrawal direction, the air accumulated between the tube main body 64 and the intestine wall is suctioned. Thus, compression can be prevented, and the insertion assisting device 60' can be smoothly operated in the withdrawal direction. Furthermore, when the suction from the ventilation openings 90 is to be stopped, the operator stops the closing of the opening 97 of the grasp portion 62 such that the duct 74 is opened to the outside and the suction is stopped.

According to the third embodiment, since the air can be suctioned from the ventilation openings 90, the withdrawal operation of the insertion assisting device 60' can be performed smoothly.

Also, according to the third embodiment, since the insertion assisting device 60' is connected to the suction device 83' through the suction tube 87' being provided within the endoscope 10', the number of long tubes exposed to the outside can be shortened, as compared with the case where the insertion assisting device 60' is directly connected to the suction device 83' (that is, the case where the connector 96' and the suction device 83' are connected through a tube). Therefore, when the insertion assisting device 60' is inserted or withdrawn, the tubes do not get in the way, and the operability of the insertion assisting device 60' can be enhanced. In the third embodiment, since the suction tube 87', which is provided within the endoscope 10' and communicates with the duct 74, is disposed within the universal cable 16, the number of cables extending from the hand operation unit 14' does not increase, and the operability of the endoscope 10' can be enhanced.

According to the third embodiment, since the liquid reservoir tank 91' is disposed in the middle of the duct between the ventilation openings 90 of the insertion assisting device 60' and the suction device 83', the liquid such as body fluid suctioned from the openings 90 can be removed into the liquid reservoir tank 91'.

Furthermore, according to the third embodiment, since the opening 97 communicating with the duct 74 is provided in the grasp portion 62 of the insertion assisting device 60', the suction from the ventilation openings 90 can be performed and stopped by closing the opening 97 and releasing the closing of the opening 97. Therefore, the operability of the insertion assisting device 60' can be further enhanced.

In the third embodiment, the on/off operation of the suction is switched by closing the opening 97 of the grasp portion 62. Instead of the opening 97, an opening and closing valve may be provided in the duct 74 such that the duct 74 is opened to the atmosphere or is blocked from the atmosphere by the opening and closing valve.

Figure 14:
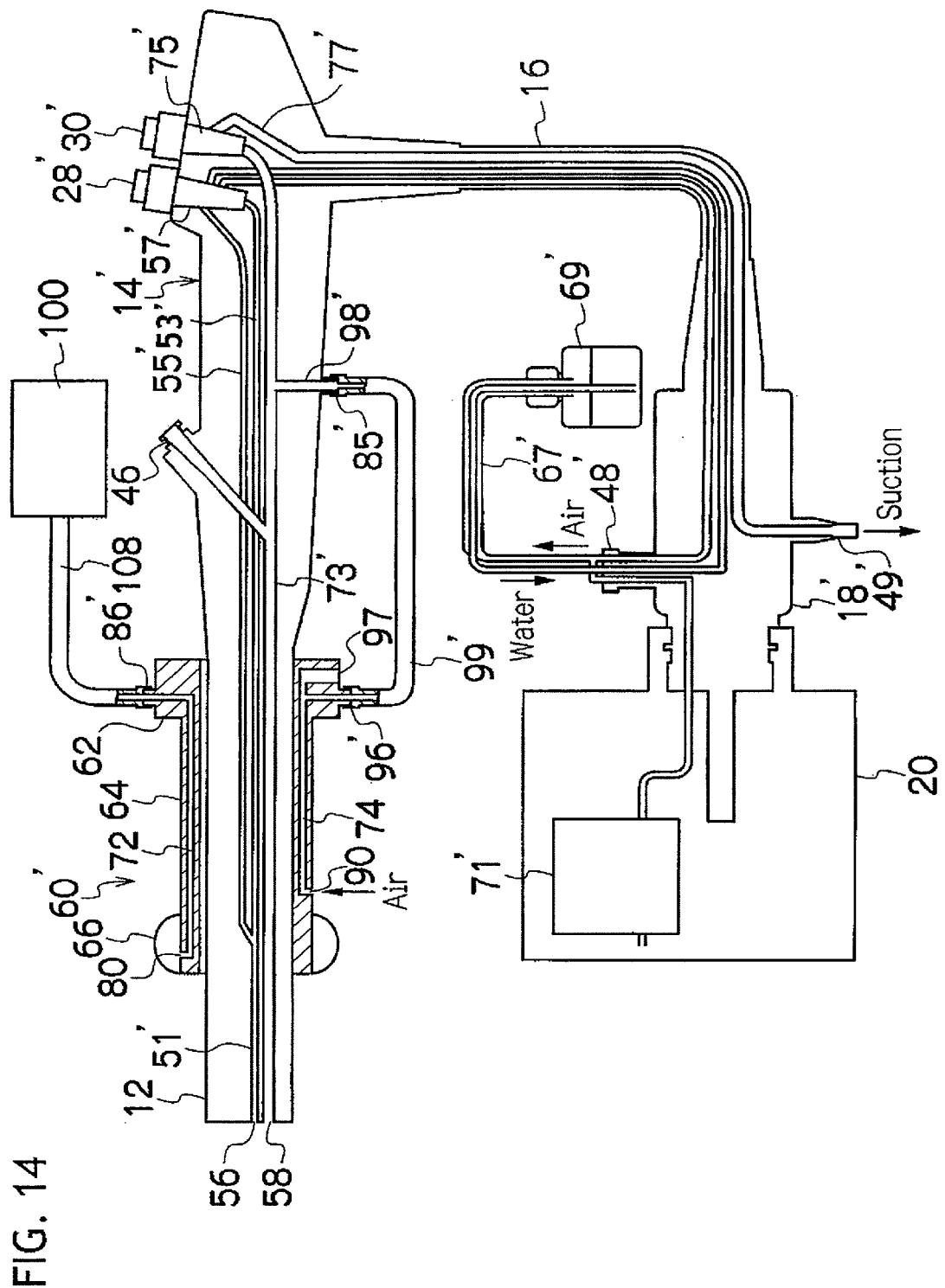
FIG. 14 is a diagram showing the duct configuration of the endoscope apparatus according to the fourth embodiment of the invention.

Next, a fourth embodiment of the invention will be described. FIG. 14 is a diagram showing the duct configuration of an endoscope apparatus according to the fourth embodiment of the invention. In the endoscope apparatus according to the fourth embodiment shown in FIG. 14, the connector 85' provided in the hand operation unit 14' of the endoscope 10' is connected to a tube 98', and the tube 98' is connected to the forceps tube 73', which is a forceps channel. As the connector 85' of the hand operation unit 14' and the connector 96' of the grasp portion 62 of the insertion assisting device 60' are connected to each other through the tube 99', the duct 74 of the insertion assisting device 60' communicates with the forceps channel. Therefore, as a suction force is applied to the forceps tube 73' by operating the suction button 30', the suction from the ventilation openings 90 can be performed. In this case, a three-way valve may be provided in the connection position between the tube 98' and the forceps tube 73' such that whether to connect the valve 75' to the forceps port 58 or the connector 85' is selected by the three-way valve.

Even in the fourth embodiment configured in such manner, the air can be suctioned from the ventilation openings 90. Therefore, the insertion and withdrawal operation of the insertion assisting device 60' can be performed smoothly. Furthermore, according to the fourth embodiment, the forceps channel of the endoscope 10' is used to perform the air suction from the ventilation openings 90. Therefore, the duct or suction connector within the endoscope 10' does not need to be newly provided.

In the above-described fourth embodiment, the switching of the suction is performed by the three-way valve (not shown). Similar to the third embodiment, however, the opening 97' (refer to FIG. 12) may be formed in the grasp portion 62 such that the switching of the suction is performed by closing the opening 97. Furthermore, in FIG. 14, the tube 98' may be directly connected to the valve 75', and the valve 75' may be used as a two-step push operation mechanism. In this case, when the valve 75' is not operated, the suction tube 77' communicates with the outside. When a one-step push operation of the valve 75' is performed, the suction tube 77' communicates with the forceps tube 73'. When a two-step push operation of the valve 75' is performed, the suction tube 77' communicates with the tube 98'. Accordingly, the suction from the forceps port 58, the suction from the openings 90, and the stop of the suction operations can be performed by the suction button 30'.

Also, instead of the connector 85' of the hand operation unit 14', the tube 99' may be connected to the forceps insertion portion 46 so as to be connected to the forceps channel. In this case, a member having two insertion ports may be used as the forceps insertion portion 46.

In the above-described first to fourth embodiments, the ventilation holes (openings 90) are formed on the outer circumferential surface of the tube main body 64. However, the ventilation holes may be formed on the distal-end surface of the tube main body 64. Furthermore, the ventilation holes may be formed in both of the outer circumferential surface and the distal-end surface of the tube main body 64. In this case, as shown in FIG. 10, the duct 74' communicating with the opening (not shown) of the distal-end surface may be provided separately from the duct 74 communicating with the openings 90 of the outer circumferential surface such that the duct 74' is disposed in the opposite side to the duct 72 and in the vicinity of the duct 74.

In the first to fourth embodiments, the single-balloon endoscope apparatus has been exemplified, in which the balloon 66 is mounted on only the insertion assisting device 60 (60'). However, another balloon which can swell and contract may be mounted on the insertion portion 12 of the endoscope 10 (10') such that the endoscope apparatus is used as a double-balloon endoscope apparatus. In this case, the distal end of the insertion portion 12 can be inserted into a deep portion of the intestine by repeatedly performing the following operations: an insertion operation for inserting the insertion portion 12 of the endoscope 10 (10'), a fixing operation for fixing the insertion portion 12 by inflating the balloon on the insertion portion 12, a pushing operation for pushing the insertion assisting device 60 (60') along the insertion portion 12, a grasping operation for grasping the intestine by inflating the balloon 66, and a hauling operation for hauling the insertion assisting device 60 (60).

The invention is not limited to the above-described embodiments, but various changes and modifications may be made so long as the above described advantages can be achieved. For example, any two or more of the above-described embodiments may be combined appropriately.

What is claimed is:

1. An endoscope apparatus comprising: an endoscope having an insertion portion; and an insertion assisting device having a substantially tubular shape, wherein the insertion assisting device includes:
    an insertion path into which the insertion portion of an endoscope is inserted;
    an inflatable balloon that is mounted on an outer circumference of a distal-end portion of the insertion assisting device;
    a first opening that is formed on the outer circumference of the distal-end portion of the insertion assisting device and communicates with the balloon;
    a balloon fluid duct that communicates with the first opening and is different from the insertion path;
    a ventilation hole that is formed on a distal-end surface or outer circumferential surface of the insertion assisting device;
    a ventilation duct that communicates with the ventilation hole and is different from the insertion path and from the balloon fluid duct, wherein the ventilation duct is connected to a suction device through a duct provided in the endoscope and the ventilation duct is connected to the duct provided in the endoscope through a tube, wherein
        the tube and the duct provided in the endoscope are connected to each other via a connector provided in a hand operation unit of the endoscope, and
        the tube and the ventilation duct are connected to each other via a connector provided in the grasp portion of the insertion assisting device; and
    a second opening that communicates with a portion diverging from the ventilation duct and is formed in a grasp portion of the insertion assisting device,
wherein the ventilation duct is opened to an outside through the second opening.

2. The endoscope apparatus according to claim 1, wherein the duct, which is provided in the endoscope, is inserted into an inside of a universal cable that extends from a hand operation unit of the endoscope, so as to be connected to another equipment.

3. The endoscope apparatus according to claim 1, wherein the duct, which is provided in the endoscope, is a forceps channel through which suction is performed from a forceps port formed on a distal-end portion of the insertion portion, and
the ventilation duct of the insertion assisting device communicates with the forceps channel.

* * * * *